United States Patent
Klausman et al.

(10) Patent No.: US 11,678,912 B2
(45) Date of Patent: Jun. 20, 2023

(54) MINIMALLY INVASIVE COMPRESSOR / DISTRACTOR

(71) Applicant: Astura Medical Inc., Carlsbad, CA (US)

(72) Inventors: Keith Klausman, Carlsbad, CA (US); Thomas Purcell, Carlsbad, CA (US); Joel Gambrell, Carlsbad, CA (US)

(73) Assignee: Astura Medical Inc, Irving, TX (US)

( * ) Notice: Subject to any disclaimer, the term of this patent is extended or adjusted under 35 U.S.C. 154(b) by 0 days.

(21) Appl. No.: 16/581,724

(22) Filed: Sep. 24, 2019

(65) Prior Publication Data

US 2021/0085370 A1 Mar. 25, 2021

(51) Int. Cl.
*A61B 17/70* (2006.01)
*A61B 17/02* (2006.01)

(52) U.S. Cl.
CPC .......... *A61B 17/708* (2013.01); *A61B 17/025* (2013.01); *A61B 2017/0256* (2013.01)

(58) Field of Classification Search
CPC ...... A61B 17/025; A61B 17/7077–708; A61B 2017/256
See application file for complete search history.

(56) References Cited

U.S. PATENT DOCUMENTS

| | | |
|---|---|---|
| 2005/0177173 A1 | 8/2005 | Aebi |
| 2009/0171391 A1* | 7/2009 | Hutton .............. A61B 17/7082 606/246 |
| 2010/0004695 A1* | 1/2010 | Stad .................... A61B 17/708 606/86 A |
| 2011/0106082 A1 | 5/2011 | Kave |
| 2012/0271308 A1 | 10/2012 | Dominik |
| 2014/0277198 A1* | 9/2014 | Stad .................... A61B 17/7002 606/86 A |
| 2015/0066088 A1* | 3/2015 | Brinkman .......... A61B 17/7077 606/264 |
| 2015/0351814 A1* | 12/2015 | McClintock ......... A61B 17/708 606/279 |
| 2018/0256215 A1* | 9/2018 | Obeid ................ A61B 17/7004 |
| 2018/0271566 A1* | 9/2018 | Fischer ............. A61B 17/7085 |
| 2019/0110785 A1* | 4/2019 | Serokosz .......... A61B 17/7077 |
| 2019/0209080 A1* | 7/2019 | Gullotti ............. A61B 17/7076 |
| 2020/0093614 A1* | 3/2020 | Arramon ............... A61B 90/03 |

OTHER PUBLICATIONS

International Search Preliminary Report on Patentability in PCT Application No. PCT/US2019/052803 dated Apr. 24, 2020.
Ternational Search Report and Written Opinion in PCT Application No. PCT/US2019/052803 dated Nov. 15, 2019.

* cited by examiner

*Primary Examiner* — Eduardo C Robert
*Assistant Examiner* — Steven J Cotroneo
(74) *Attorney, Agent, or Firm* — Michael R. Shevlin

(57) ABSTRACT

A compressor/distractor instrument that provides internal set screw engagement for threaded reduction capabilities while also providing bending support of the screw extenders during compression or distractor manipulation. Threaded reduction is performed by engaging compressor/distractor support tubes at the proximal end with a compressor/distractor driver. A removable locking pull pin secures the left and right handles of the compressor/distractor driver together during use, and removal of the pin releases the compression and tension built up in the device for ease of removal.

15 Claims, 4 Drawing Sheets

MINIMALLY INVASIVE COMPRESSOR / DISTRACTOR

CROSS-REFERENCE TO RELATED APPLICATIONS

This application claims the benefit of U.S. Provisional Application No. 62/735,823 filed Sep. 24, 2018, which is incorporated herein by reference.

FIELD

The present invention relates generally to the field of surgery, and more specifically, to a compressor/distractor for use in spinal fusion surgery.

BACKGROUND

In many surgical spinal procedures pedicle screws are inserted into the vertebrae of the defective region and spinal fixation rods are used to rigidly fix the vertebrae relative to one another between the screws. Typically, screw extenders may attach to the screws and are used to assist with insertion of the spinal rods. In many cases, adjustment of the screws is needed to put the spine in the correct position for the spinal rod. This is usually done by applying compression and/or distraction forces of a compressor/distractor instrument to vertebrae via the screw extenders in the defective region.

Current minimally invasive surgery compressor/distractor instruments do not engage with the set screw and have internal threaded reduction capabilities.

Current minimally invasive surgery compressor/distractor instruments do not have an internal threaded reduction feature that also provides bending support to the screw extenders or pedicle screws.

Current minimally invasive surgery compressor/distractor instruments do not have a convenient and secure way of releasing compression or tension built up within the device following anatomical manipulation.

While there are instruments that exist for applying these forces to the spine, many have some drawbacks.

Some compressor/distractor instruments require a separate driver to be inserted down through the implant or screw extender to access the set screw.

Some compressor/distractor instruments provide bending support to the screw extender or implant exteriorly.

Some compressor/distractor instruments utilize a compression/tension release but lack a locking feature.

Some problems with these are:
The use of additional instruments and steps is inefficient and potentially leads to complications.
Exterior support of the screw extenders require a larger incision.
Hinge pins without a locking feature are susceptible to disassembly.

Accordingly, there remains a need for instruments and methods that provide solutions to the problems of current systems. The present invention is directed toward meeting these needs.

SUMMARY

The present invention is directed to a minimally invasive surgery compressor/distractor instrument that provides internal set screw engagement for threaded reduction capabilities while also providing bending support of the screw extenders during compression or distractor manipulation. Threaded reduction is performed by engaging compressor/distractor support tubes at the proximal end with a compressor/distractor driver. A removable locking pull pin secures the left and right handles of the compressor/distractor driver together during use, and removal of the pin releases the compression and tension built up in the device for ease of removal.

DETAILED DESCRIPTION

Some of the current compressor/distractor instruments require a separate driver to be inserted down through the implant or screw extender to access the set screw. Other compress/distractor instruments provide bending support to the screw extender or implant exteriorly. Still others utilize a hinge pull pin style compression/tension release but lack a locking feature.

The present invention addresses these problems by using support tubes that provide two functions, the first is the compressor/distractor instrument provides strength internally to the tower or implant during compression or distraction manipulation and to also engage the set screw for reduction and tightening/loosening purposes.

The compressor/distractor instrument utilizes support tubes are positioned internally in the screw extenders.

The compressor/distractor instrument includes a pull pin that utilizes a ball lock mechanism that secures the hinged handles together. A spring loaded push button releases the ball and allows the pin to be removed, allowing the handles freedom for removal from the tower or implant.

Figure 2:
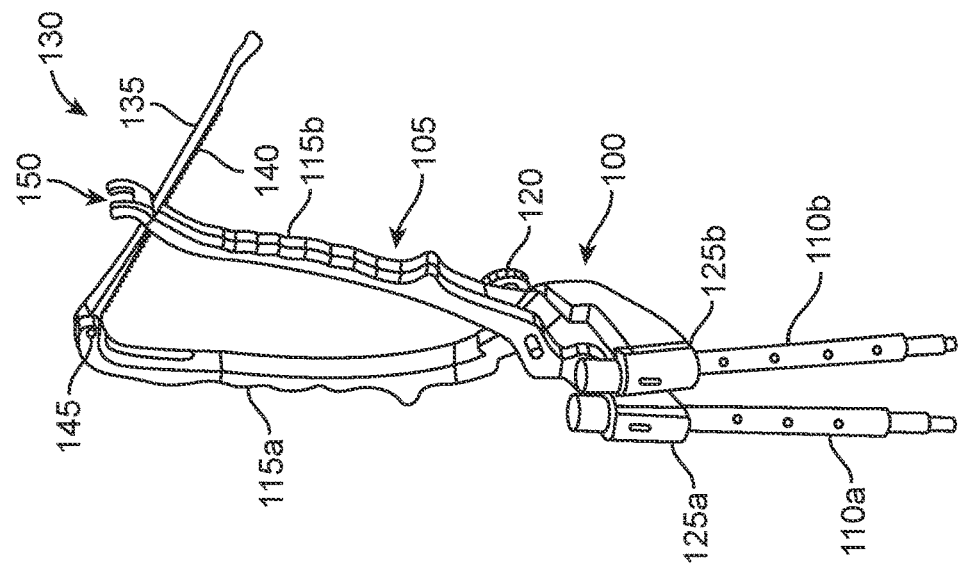
FIGS. 1 and 2 are perspective views showing ne embodiment of a minimally invasive surgery (MIS) compressor/distractor instrument.
Figure 1:
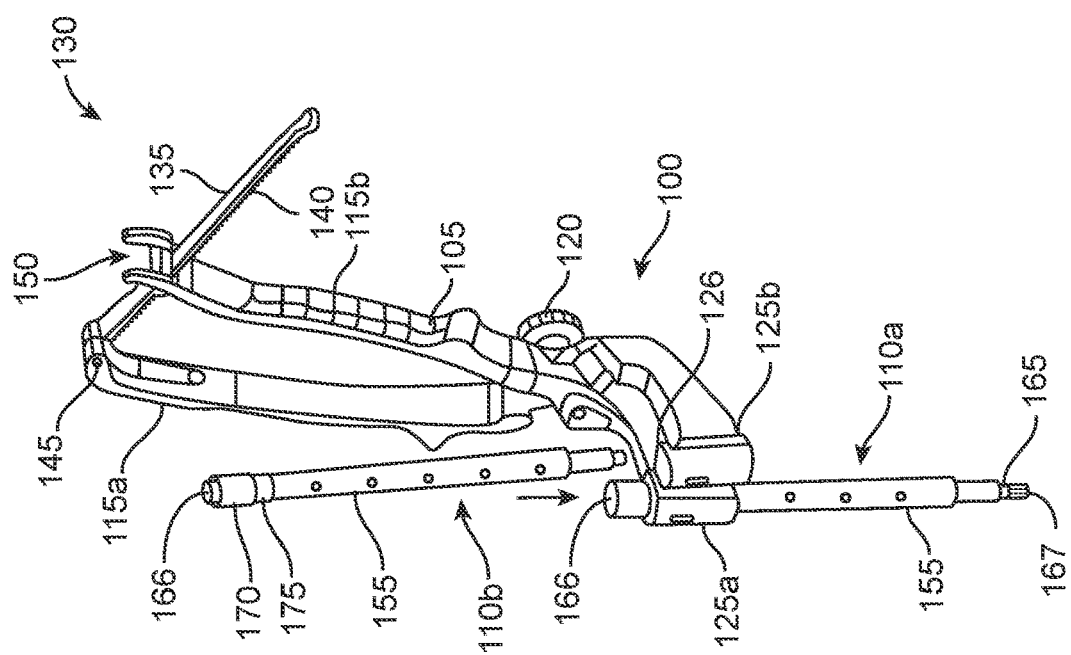

FIGS. 1 and 2 show one embodiment of a minimally invasive surgery (MIS) compressor/distractor instrument 100 comprising a compressor/distractor device 105 and compressor/distractor support tubes 110a, 110b.

Figure 3:
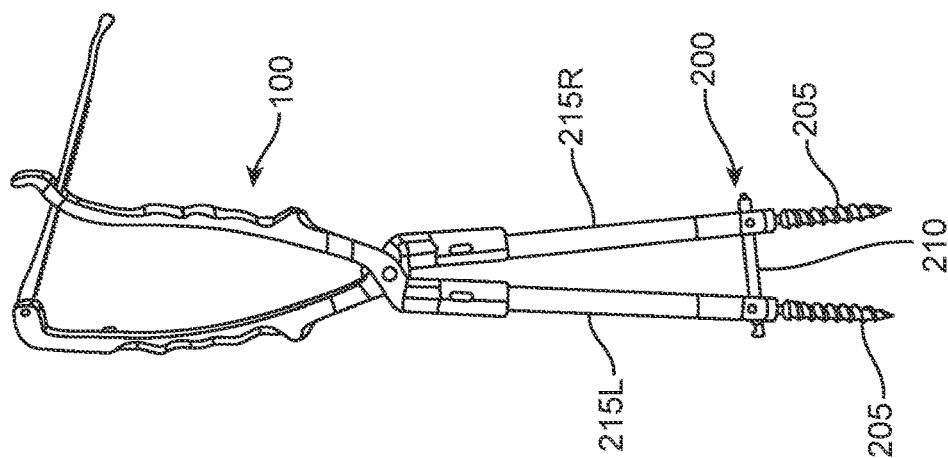
FIG. 3 is a perspective view showing the compressor/distractor instrument engaged with a spinal fixation system 200.

The compressor/distractor device 105 includes left and right handles 115a, 115b that are pivotably hinged together by a removable locking pin 120. The distal ends of the left and right handles 115a. 115b include left and right tube engagement arms 125a, 125b having an opening 126 configured to receive the compressor/distractor support tubes 110a, 110b and pedicle screw extenders 215 (see FIG. 3).

The compressor/distractor support tubes 110a, 110b include a tubular body 155 having a central lumen 160 housing a screw driving shaft 165. The body 155 is configured to fit within the openings 126 on the tube engagement arms 125a, 125b. The tubular body 155 further includes a proximal cap 170 having a male threaded portion 175 configured to engage female threads on the pedicle screw extenders 215 on the support tube openings of the engagement arms 125a, 125b. The compressor/distractor support tubes 110a, 110b are also configured to fit within screw extensions 215 and provide bending support screw extensions 215 during compression or distractor manipulation (see FIG. 3).

The compressor/distractor device 105 further includes a locking feature 130 on the proximal end of the left and right handles 115a, 115b being configured to lock the left and right handles 115a, 115b at a desired position. In the embodiment shown, the locking feature 130 comprises a locking arm 135 having plurality of teeth 140 pivotably attached 145 to the proximal end of left arm 115a. The proximal end of the right arm 115b includes an arm lock 150 configured to releasably engage the locking arm 135 and the teeth 140 to lock the left and right handles 115a, 115b movement of the compressor/distractor device 105 during compression or distraction. The locking arm 135 and arm lock 140 are also configured to disengage when needed so that the left and right handles 115a, 115b can be moved away from each.

FIGS. 3-7 show the compressor/distractor device 105 in use with a spinal fixation system 200 having pedicle screws 205 attached to two or more vertebrae (not shown) coupled to a fixation rod 210. Screw extenders 215 are removably attached to the pedicle screws 205 to assist in assembling and adjusting the spinal fixation system 200. The screw extenders 215 include a tubular body with a central opening or lumen extending through the body. The proximal end of the screw extenders 215 include female threads. The compressor/distractor support tubes 110a, 110b are sized to fit within the lumen and the male threads 175 engage the female threads to hold the support tubes in place and provide bending support of the screw extenders 215 during compression or distractor manipulation of the compressor/distractor device 105.

The pedicle screws 205 include a body member or head 220 that includes a U-shaped channel or slot 225 to accept the fixation rod 210. A set screw 230 is used to threadably engage the body member 220 of the screw assembly to secure the fixation rod 210 within the body member 220.

The proximal end 166 of the screw driving shaft 165 is configured to engage a screw driver or other tool 300. The distal end of the screw driving shaft 167 is configured to engage and rotate the set screw 230 to reduce and seat the fixation rod 210 in the U-shaped channel or slot 225 of the screw head 220.

With this design, the compressor/distractor support tubes 110a, 110b provide internal set screw engagement for threaded reduction capabilities of the rod, while also providing bending support of the screw extensions during compression or distractor manipulation of the compressor/distractor device 105.

In operation, the compressor/distractor support tube 110 is slide into the top of the openings 126 to the support tube engagement arms 125a, 125b compressor/distractor 105 and the screw extenders 215 are slid into the bottom of the openings 126. The male threads 175 of the compressor/distractor support tubes 110 are then coupled to the female threads of the screw extenders 200. The distal end 167 of the screw driving shaft 165 are configured to engaged with the set screws 225.

The left and right handles 115a. 115b of the compressor/distractor device 105 are then moved to compress or distract the screw extenders 200, with the compressor/distractor support tubes 110 providing support for the screw extenders 200. Once in the correct position, the locking feature 130 locks the left and right handles 115a. 115b in place.

Figure 4:
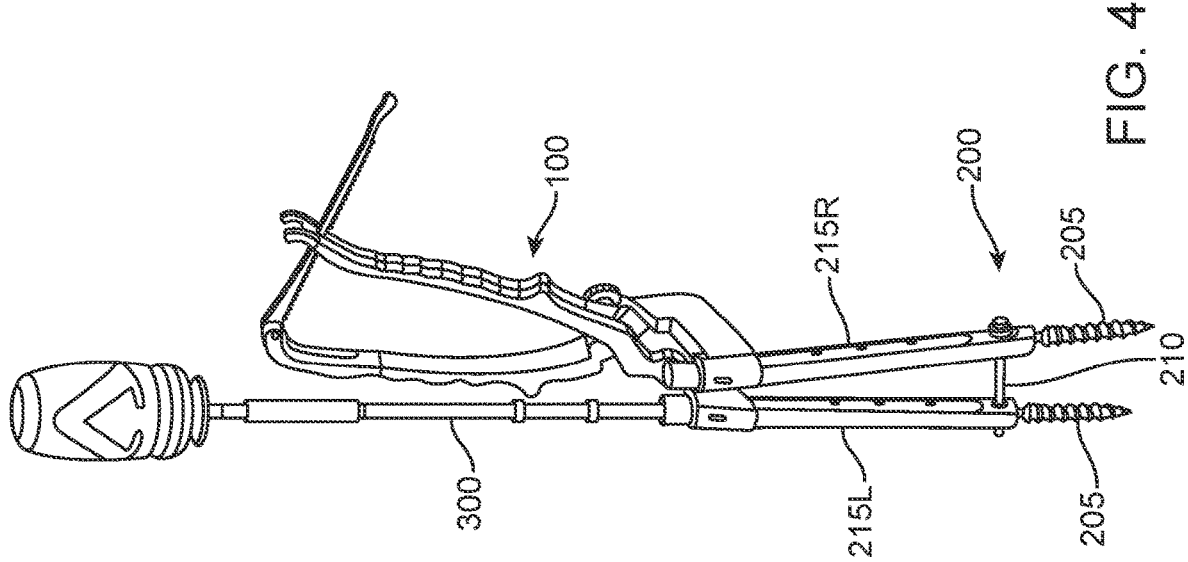

FIG. 4 shows a screwdriver or other instrument 300 coupled to the proximal end 166 of the first screw driving shaft 165 to rotate the set screw 230 to reduce the fixation rod 210 into the u-shaped channel 225 of the body member 220 and lock the fixation rod in place.

Figure 5:
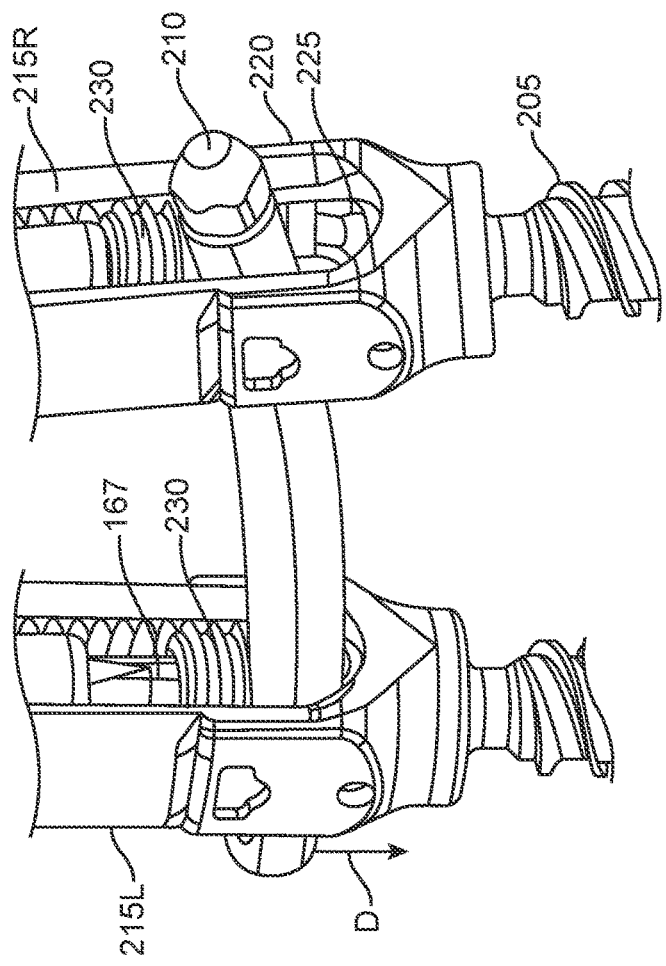
FIGS. 4-7 are views showing the operation of the compressor/distractor instrument.

FIG. 5 shows the fixation rod reduction on the left tube. The inside lumen of the left screw extension 215L and screw head 220 include female threads configured to engage male threads of the set screw 230. For rod reduction, the distal end 167 rotates the set screw 230 down the threads, which pushes the fixation rod 210 downward D into the U-shaped channel 225.

Figure 6:
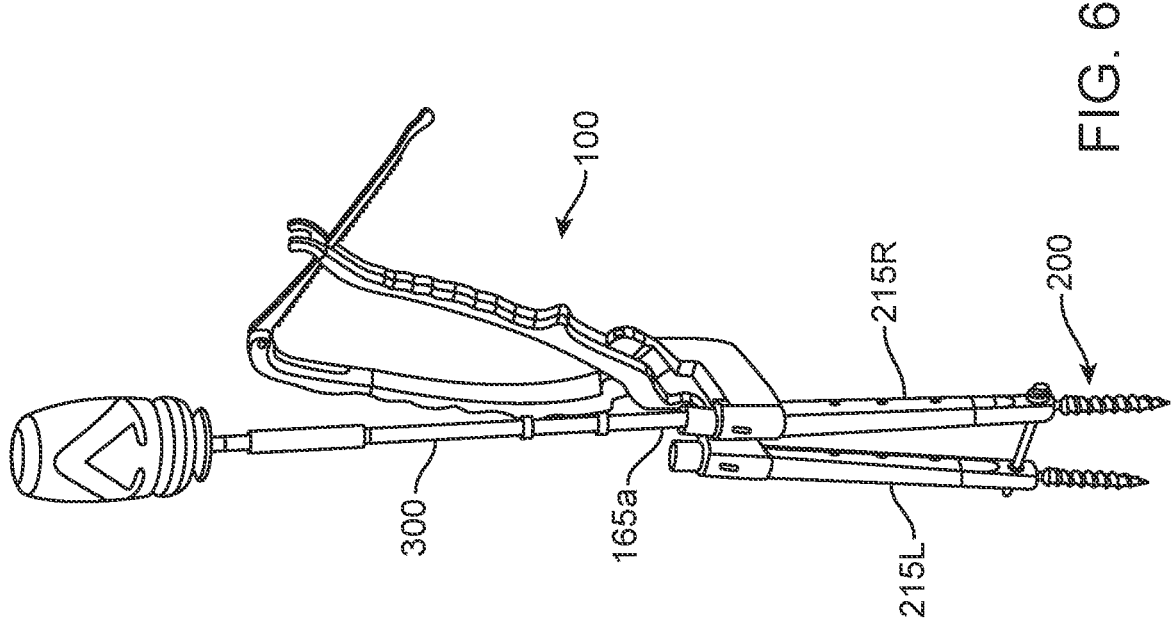

FIG. 6 shows the screwdriver 300 coupled to the proximal end 166 of the second screw driving shaft 165 to rotate the set screw 230 to reduce the fixation rod 210 into the u-shaped channel 225 of the body member 220 and lock the fixation rod in place.

Figure 7:
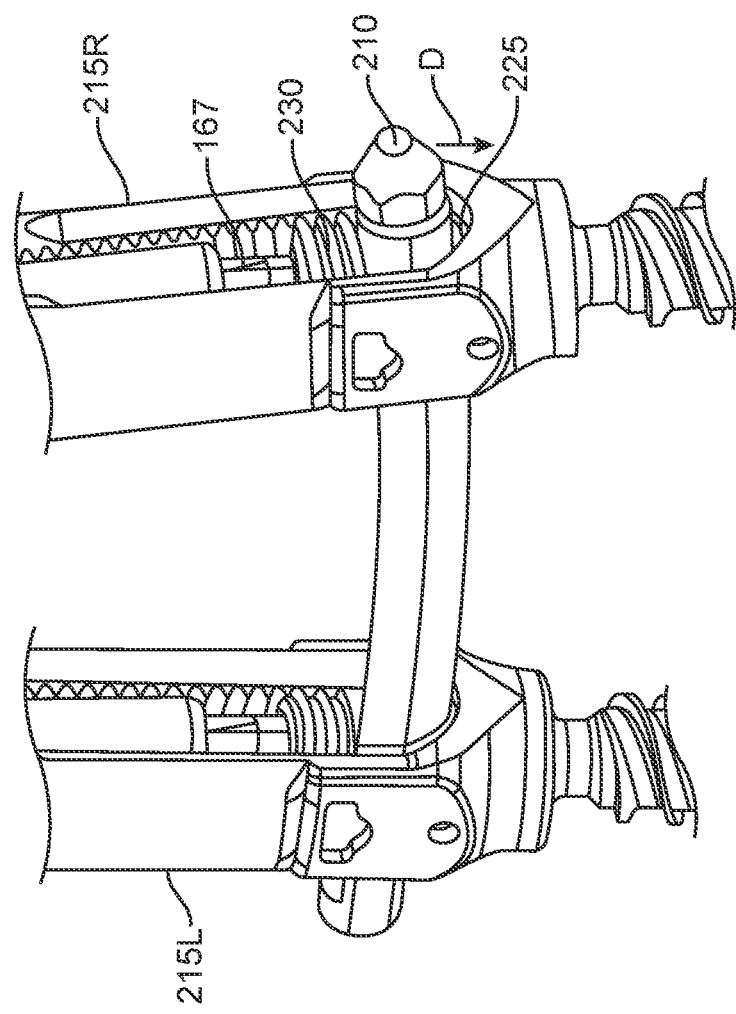

FIG. 7 shows the fixation rod reduction on the right tube. The inside lumen of the right screw extension 215R and screw head 220 include female threads configured to engage male threads of the set screw 230. The distal end 167 rotates the set screw 230 down the threads, which pushes the fixation rod 210 downward D into the U-shaped channel 225.

In FIG. 7, the fixation rod 225 had been reduced into the screw heads 220 and is fixed in place. The compressor/distractor instrument 100 may now be removed.

Figure 8:
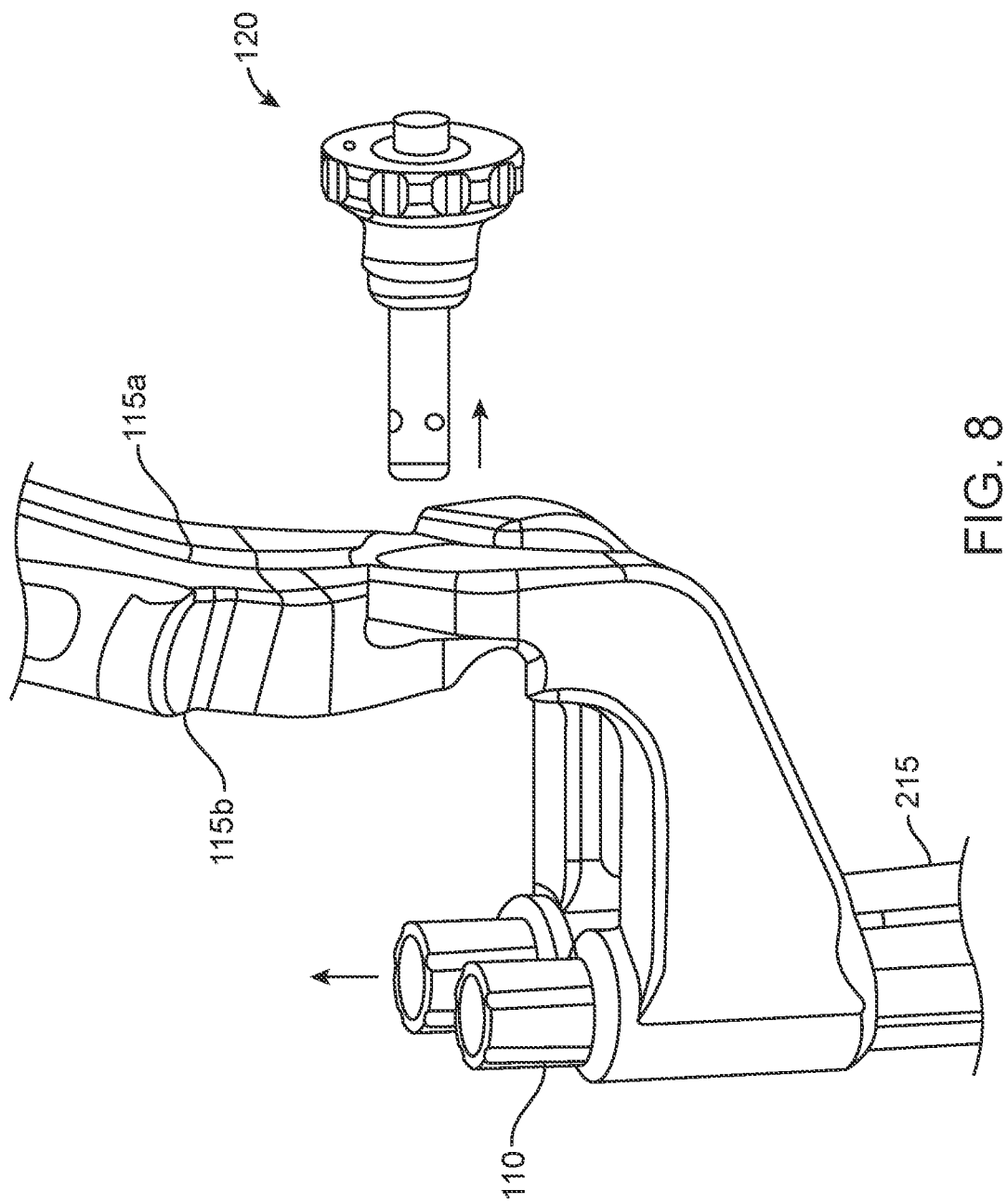
FIG. 8 is an enlarged perspective view showing details of a hinge pull pin of the compressor/distractor instrument.

In one embodiment, shown in FIG. 8, the pull pin 120 may be pulled so that the left and right handles 115a, 115b are separated. The pull pin 120 may utilize a ball lock mechanism that secures the hinged handles together. A spring loaded push button releases the ball and allows the pin to be removed, allowing the handles freedom for removal from the tower or implant. Once the pull pin 120 is removed, the compressor/distractor support tubes 110a, 110b are disengaged from the screw extensions 215. The compressor/distractor support tubes 110a, 110b are pulled from the screw extensions, and the left and right handles 115a, 115b handles removed.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. A compressor/distractor instrument comprising:
   a compressor/distractor device having left and right handles pivotably hinged together by a removable locking pin, the distal ends of the left and right handles include left and right tube engagement arms having an opening;
   pedicle screw extenders having a tubular body with a central opening or lumen extending through the body;
   left and right compressor/distractor support tubes configured to fit within the central opening or lumen of the pedicle screw extenders to provide bending support during compression or distraction, each support tube having:
      a tubular body having a central lumen configured to fit within the openings on the tube engagement arms;
   first and second screw driving shafts positioned within the central lumen of the left and right compressor/distractor support tubes having:

a proximal end within the support tube configured to engage a screw driver or other tool; and a distal end configured to engage and rotate a set screw to reduce a fixation rod;

a threaded portion configured to engage threads on the pedicle screw extender to hold the support tubes in place during compression or distractor manipulation.

2. The instrument of claim 1, wherein the removable locking pin includes a spring loaded push button releases a ball lock mechanism and allows the pin to be removed.

3. The instrument of claim 1, wherein the threaded portion includes male threads configured to engage female threads on the pedicle screw extender.

4. The instrument of claim 1, wherein distal ends of the left and right handles include an opening and the body being configured to fit within the opening.

5. The instrument of claim 1, wherein the compressor/distractor device further includes a locking feature coupled to left and right handles being configured to lock the left and right handles at a desired position.

6. The instrument of claim 5, wherein the locking feature is also configured to disengage when needed.

7. A compressor/distractor instrument comprising:

a compressor/distractor device having left and right handles pivotably hinged together by a removable locking pin;

pedicle screw extenders having a tubular body with a central opening or lumen extending through the body;

left and right compressor/distractor support tubes having a body and a lumen, the compressor/distractor support tubes being coupled to the left and right handles and configured to fit within the central opening or lumen of the pedicle screw extenders; and first and second screw driving shafts positioned within the left and right compressor/distractor support tube lumens and each screw driving shaft having:

a proximal end within the support tube configured to engage a screw driver or other tool; and a distal end configured to couple and rotate a set screw.

8. The instrument of claim 7, wherein the removable locking pin includes a spring loaded push button releases a ball lock mechanism and allows the pin to be removed.

9. The instrument of claim 7, wherein the compressor/distractor support tubes include a threaded portion configured to engage a threaded portion on a proximal end of the pedicle screw extender.

10. The instrument of claim 7, wherein distal ends of the left and right handles include an opening and the body being configured to fit within the opening.

11. The instrument of claim 7, wherein the compressor/distractor device further includes a locking feature coupled to left and right handles being configured to lock the left and right handles at a desired position.

12. The instrument of claim 11, wherein the locking feature is also configured to disengage when needed.

13. A compressor/distractor instrument comprising:

a compressor/distractor device having left and right handles pivotably hinged together by a removable locking pin, the distal ends of the left and right handles include left and right tube engagement arms having an opening;

pedicle screw extenders having a tubular body with a central opening or lumen extending through the body;

left and right compressor/distractor support tubes having a tubular body and a central lumen, the tubular body being configured to fit within the openings on the tube engagement arms and further configured to fit within the central opening or lumen of the pedicle screw extenders; and first and second screw driving shafts positioned within the left and right compressor/distractor support tube lumens and having a distal end configured to couple and rotate a set screw and a proximal end within the support tube configured to engage a screw driver or other tool.

14. The instrument of claim 13, wherein the compressor/distractor support tubes include a threaded portion configured to engage a threaded portion on a proximal end of the pedicle screw extender.

15. The instrument of claim 13, wherein the compressor/distractor device further includes a locking feature coupled to left and right handles being configured to lock the left and right handles at a desired position and disengage when needed.

* * * * *